United States Patent [19]

Schmidt et al.

[11] 4,363,626
[45] Dec. 14, 1982

[54] DENTAL SYRINGE

[75] Inventors: Manfred Schmidt; Gerd Hoyer; Hermann Leiberich, all of Karlsruhe; Helmut Pietschmann, Karlsbad, all of Fed. Rep. of Germany

[73] Assignee: Sybron Corporation, Rochester, N.Y.

[21] Appl. No.: 149,950

[22] Filed: May 15, 1980

[51] Int. Cl.³ ............................................. A61C 1/10
[52] U.S. Cl. ................................... 433/85; 433/100; 200/153 H
[58] Field of Search ....................... 433/80, 84, 82, 27, 433/85, 100, 99, 98; 128/224, 200.19, 229; 200/153 H; 338/32 H

[56] References Cited

U.S. PATENT DOCUMENTS

| | | |
|---|---|---|
| 2,228,169 | 1/1941 | Keogh, Jr. et al. .................. 433/80 |
| 2,412,318 | 12/1946 | Camras ........................... 200/153 H |
| 3,393,676 | 7/1968 | Kummer et al. ...................... 433/80 |
| 3,568,318 | 3/1971 | Martin ............................... 433/100 |
| 3,959,883 | 6/1976 | Walls et al. .......................... 433/99 |
| 4,216,458 | 8/1980 | Edwards .......................... 338/32 H |

FOREIGN PATENT DOCUMENTS 876138 5/1953 Fed. Rep. of Germany ...... 128/224
1227187 10/1966 Fed. Rep. of Germany ........ 433/85

Primary Examiner—Gene Mancene
Assistant Examiner—John J. Wilson
Attorney, Agent, or Firm—Theodore B. Roessel; Roger Aceto

[57] ABSTRACT

A dental syringe employs a single thumb or finger operated control member mounted on the syringe for regulating the flow of air or water or spray. The single control moves axially and vertically with respect to the syringe. Axial movement either forward or rearward from a rest position, initiates and controls the quantity of flow of air or water. Vertical movement of the control member initiates the flow of both air and water to produce a spray.

7 Claims, 4 Drawing Figures

DENTAL SYRINGE

BACKGROUND OF THE INVENTION

The present invention relates generally to a dental syringe and more particularly to such a syringe wherein the valves controlling the flow of a fluid medium, such as air, water or an air-water spray are located remote from the syringe.

A dental syringe is an instrument well known in the art. Such an instrument is merely the hand held terminus of various fluid supply lines and is used by the dentist to direct a stream of air, water, or an air-water spray to the tooth. Normally, such an instrument incorporates the various valves for controlling the flow of the medium through the syringe. The usual case is to provide at least two valves within the syringe and then to have a separate operating mechanism attached to each of the valves. In this way, the operator can use one of the mechanisms to select and control the flow of air, use the second mechanism to initiate and control the flow of water and use both mechanisms simultaneously to obtain an air-water spray. Typical of such devices are those illustrated, for example, in U.S. Pat. Nos. 3,401,691, 3,511,235 and 3,593,423.

In the present invention, the syringe is provided with a single operating means for controlling the flow of either air, water or selecting a spray. The single means not only selects the particular fluid medium desired, but also the rate of flow. In the present invention, the valves for controlling flow are located remote from the hand held syringe and are electrically connected to the flow control means within the syringe. In this fashion, the overall size of the syringe is greatly reduced, which facilitates the manual manipulation of the syringe and also allows the syringe to have a more pleasing and aesthetic appearance.

SUMMARY OF THE INVENTION

The present invention may be characterized in one aspect thereof by the provision of a dental syringe including a hand held housing having two fluid passages, each of them terminating in a nozzle for directing a medium such as air and water or an air-water spray onto a tooth. The flow controlling valves are located remote from the housing and are electrically connected to switches and rate control means within the housing. Mounted to the housing is a single, thumb or finger manipulated member which has two degrees of motion, including back and forth axially with respect to the housing and vertically towards and away from the housing. This member is mechanically connected to the switch and flow control means within the housing, so that the operation of the member in a selected one in the degrees of motion operates to select the medium desired and to control the rate of flow of that medium.

DESCRIPTION OF THE PREFERRED EMBODIMENTS

Figure 1:
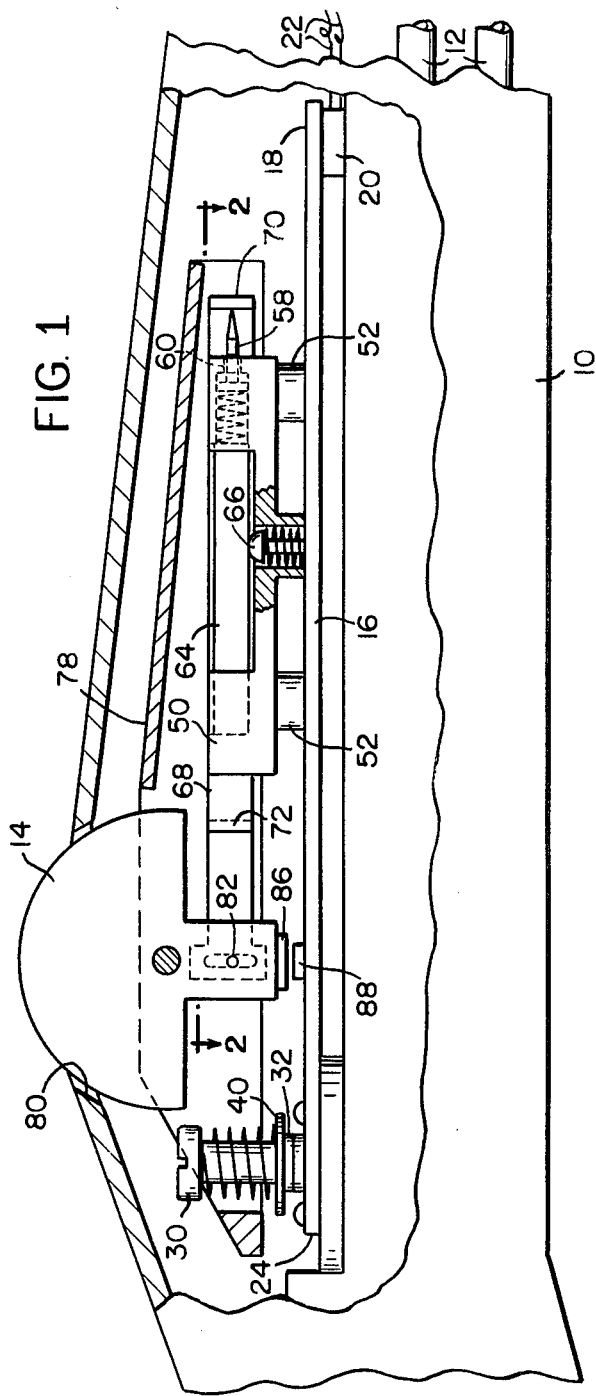
FIG. 1 is a side elevation view, partly broken away and in section showing a portion of the dental syringe of the present invention.

Referring to the drawings, FIG. 1 shows a portion of a dental syringe housing 10. The housing is of a size which can be held in the hand of the dentist or his assistant. Within this housing are fluid conduits 12. These conduits form no part from the present invention and it is sufficient merely to say that one end of this conduit, to the right as viewed in FIG. 1, are connected to the supply lines for air and water respectively. The other end of the conduits, to the left as viewed in FIG. 1, communicates with nozzles for directing air, water or air-water spray onto a tooth.

It is important, for purposes of the present invention, to note that there are no mechanical valves within the conduits 12 for controlling the flow. Such valves (not shown) are located at some point remote from syringe 10. These valves (not shown) are electrically connected to switches and transducers located within the syringe housing 10. These switches and transducers for selecting and operating one or more of the remote valves are connected to a thumb or fingertip manipulated control member 14 mounted on the housing so that selection and control of flow of either air, water or an air-water spray is accomplished by manipulation of a single member. In the embodiment shown, this member is in the form of a wheel but may take other shapes.

Within syringe housing 10 of FIG. 1, is a printed circuit board 16. This circuit board is fixed at one end 18 to the housing by a spacer element 20 which is flexible for purposes set out hereinbelow. All the necessary electrical connections to and from the printed circuit board can be made through spacer 20 to the electrical conductors 22. These conductors extend to the rear of the syringe and connect to the remote flow control valves (not shown).

Figure 4:
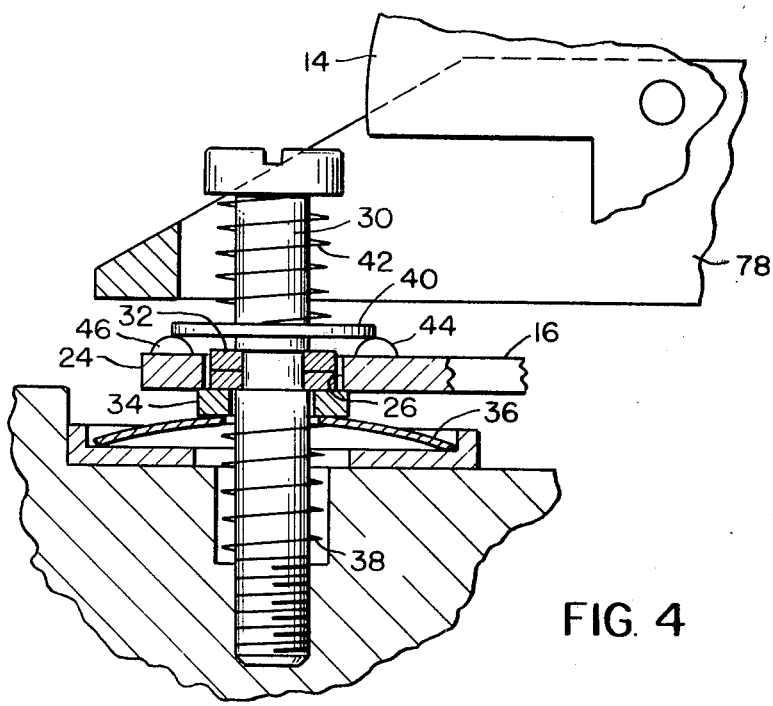
FIG. 4 is an enlarged view, partly broken away and in section of the syringe spray contact.

The other end 24 of the printed circuit board is free to move vertically between defined limits. In this respect, the printed circuit board has a clearance opening 26. Extending through this clearance opening, as best seen in FIG. 4, is a stud 30. The stud is threaded for attachment to housing 10. Fixed about stud 30 is a collar 32 which functions as a stop as set out hereinbelow.

Slidably disposed about the stud and below collar 32 is a washer 34. The washer is biased upwardly and against the stop through the action of a spring washer 36 and a coil spring 38 which is biased between the spring washer and fluid housing 10. It should be noted that the outside diameter of washer 34 is larger than the inside diameter of opening 26 in the printed circuit board so that the upward movement of washer 34 also moves the end 24 of printed circuit board. The limit of this upward movement occurs when washer 34 engages collar 32 as shown in FIG. 4.

Also slidably disposed about stud 30, but above collar 32 is a contact ring or washer 40. The washer is biased in a downward direction by the action of a spring 42 which extends between washer 40 and the head of stud 30. With the printed circuit board 16 at its highest position shown in FIG. 4, washer 40 engages two contacts 44 and 46 on the printed circuit board. In this way, the washer completes a circuit between the two contacts for purposes set out hereinbelow.

On the other hand, when the printed circuit board 16 is pushed downward against the bias of spring 38, washer 40 will follow this downward movement until it engages against the collar 32. Thereafter, any further movement of the printed circuit board will separate contacts 44, 46 from the washer as shown for example in FIG. 1, thereby opening the circuit between the two contacts. Due to the strength of spring 38, the position shown in FIG. 4 is the normal position of the printed circuit board and the printed circuit board will return to this position each time the downward force on the board is released.

Referring, again, to FIG. 1, the present invention utilizes two electro-mechanical switches and a transducer all contained in a single member 50 which is attached to the circuit board by any conventional means such as studs 52.

Figure 2:
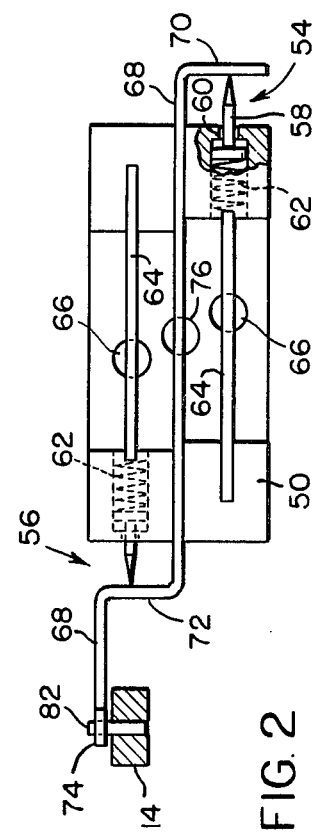
FIG. 2 is a view taken along lines 2—2 of FIG. 1.

As best seen in FIG. 2, the two electro-mechanical switches, generally indicated at 54 and 56, are located at each end of member 50. The switches are identical in construction so that the structure and operation of only switch 54 will be described in detail. Each switch includes a sliding pin 58 which extends through an opening 60 in an end face of member 50. The pin is biased outwardly from member 50 by a spring 62 which is disposed between the pin and a fixed electrical conductor 64. It should be appreciated that conductor 64 is electrically connected to the printed circuit board 16 through spring biased contact pin 66 (FIGS. 1 and 2).

Slidably supported by member 50 is a slide bar 68. This bar has two bent sections at 70 and 72, each bent section acting as a contact panel for the contact pin 58 of switches 54, 56 respectively. Moreover, the action of the two springs 62 acting on the bent sections 70, 72 through contact pins 58, maintain the slide bar at a centered or neutral position as shown in the Figures. With this arrangement, any movement of the slide bar, as for example, to the left as viewed in the figures will cause bent section 72 to leave or break contact with the sliding pin 58 of switch 56. Since pin 58 of switch 54 is biased outward and against bent section 70, the continued movement of slide bar to the left will maintain the electrical contact between bar 68 and pin 58 of switch 54.

Slide bar 68 between bent sections 70 and 72 (FIG. 2) is electrically connected to the printed circuit board by means of at least one spring biased contact pin 76. Thus, there is provided two normally closed contacts, each consisting of bent sections 70, 72 and the contact pin 58 of switches 54, 56 respectively. Both normally closed contacts are connected to the p.c. board 16 and can be alternately opened by moving slide bar 68 to the left or right. The opening of one contact results in the activation of the appropriate air or water valve (not shown) located at some point remote from the dental syringe to permit the flow of the selected fluid through the proper conduit 12.

The particular shape of slide bar 68 with its double bent sections 70 and 72 permit the operation of either switch 54 or switch 56. FIG. 2 clearly illustrates that movement of slide bar 68 to the left will operate switch 56, whereas movement of the slide bar to the right will operate switch 54. Motion of slide bar 68 to the left or right, is accomplished by manipulation of control member 14. This control member 14, as shown is in the form of a wheel journaled to a support member 78 carried by printed circuit board 16. The wheel extends upwardly through an opening 80 in the syringe housing 10 so that the dentist can manipulate the wheel with his thumb or fingertip. Rotation of wheel 14 drives an off center pin 82 back and forth. This pin is captured in an elongated vertical slot 84 formed in the end 74 of the slide bar.

With this arrangement, then, rotation of the wheel will slide bar 68 to the left or right as viewed in the figures so as to operate the selected switch 56 or 54 respectively and its associated air or water valve.

In addition to operating switches 54 and 56, slide bar 68 also operates a transducer element which generates an electrical signal proportionate to movement of the control member 14. This signal is used to control the opening of the selected air or water valve. Thus, while switch 54 or 56 determines which valve, either air or water, is to be operated, the transducer element as described hereinbelow determines the quantity of flow by regulating the amount of the valve opening.

Figure 3:
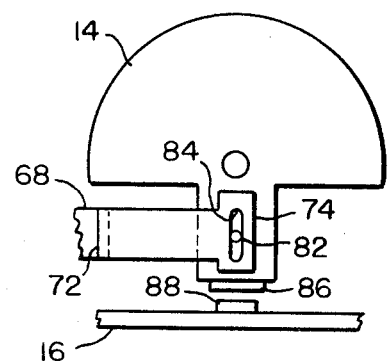
FIG. 3 is an elevation view showing the opposite side of a portion of the syringe operating mechanism shown in FIG. 1.

There are several types of transducer elements that can be provided, as for example, a rheostat. In the preferred embodiment, however, this transducer element takes the form of a Hall effect device. Hall effect devices are well known. In such a device, the electrical signal generated is directly proportional to a magnetic field to which the device is exposed. To adapt a Hall effect device for use in the present invention, control member 14 is provided with small permanent magnet 86 (FIGS. 1 and 3). Incorporated into the p.c. board just below magnet 86 is the Hall effect device 88. With this arrangement, movement of the control member 14 to the left or right will carry permanent magnet 86 across the Hall effect device 88 changing the electrical output of the device. This change in electrical output is communicated through the printed circuit board to the remote valve control mechanism (not shown). The farther control member 14 is rotated, the greater the change in the electrical output of Hall effect device 88 and consequently, the more the selected valve (air or water) is opened.

In operation, the dentist simply rotates control member 14 clockwise or counterclockwise depending upon which medium (air or water) is desired. The rotation of control member 14 is translated to linear movement of slide bar 68 by operation of the pin 82 in slot 84. Movement of slide 68 either to the left or the right will operate either switch 54 or 56. Movement of the control member in either direction also will produce a linear change in the electrical output characteristic Hall effect device 88. In this fashion, the dentist can select and control the flow of either air or water through the syringe. When the control member is released, the operation of springs 62 will automatically return slide bar 68 to its centered or neutral position.

Should the dentist desire to use an air-water spray, he simply pushes down on control member 14. This moves the printed circuit about its connection 20, so that end 24 of the circuit board moves from the position shown in FIG. 4 to the position shown in FIG. 1. Moving the circuit board in this fashion, opens the circuit across pins 44, 46 as set forth hereinabove, so that both of the remote air and water valves are open simultaneously to produce an air-water spray. In this regard, the separate streams of air and water leaving the syringe will be mixed in a manner known in the art to produce the spray. Release of the force on control member 14 will allow coil spring 38 and spring washer 36 to return the member to the neutral position thereby terminating the spray.

The dental syringe of this invention as described hereinabove, provides a simple and efficient means by which the dentist can select and control the flow of air, water or a spray. Furthermore, this selection and control is accomplished by the manipulation of a single control element.

We claim:

1. A dental syringe including means for selecting and controlling the flow of air, water and spray from the syringe comprising:
   (a) a hand held housing;
   (b) a support within said housing;
   (c) a movable operator carried by said support, said operator being selectively movable along a path of either side of a neutral position;
   (d) a control member journaled to said support, at least a portion of said control member extending through said housing for manipulation by a finger or thumb of the hand holding the syringe;
   (e) said operator having an elongated opening in one end extending generally normal to the path traveled by said operator;
   (f) an off center pin on said control member captured in said elongated opening so that movement of said control member through a limited arc length about said journal drives said pin and moves said operator to one side or another of a neutral position;
   (g) a pair of switches carried by said support and adapted for operative connection to air and water control valves located remote from the syringe, said switches being located on opposite sides of the neutral position of said operator so that movement of said operator in a selected direction from its neutral position will operate a selected one or another of said switches to permit the opening of a selected one of the remote air and water control valves;
   (h) means associated with said operator for generating an electrical signal which varies in proportion to the distance moved by said operator from its neutral position, said signal being utilized to determine the amount of the opening of the selected control valve; and
   (i) bias means urging said operator to its neutral position.

2. A dental syringe including means for selecting and controlling the flow of air, water and spray from the syringe comprising:
   (a) a hand held housing;
   (b) a support hinged at one end to said housing so that a second end of said support can move vertically between first and second limits of travel with respect to said housing;
   (c) a movable operator carried by said support, said operator being selectively movable along a path to either side of a neutral position;
   (d) a pair of switches carried by said support and adapted for operative connection to air and water control valves located remote from the syringe, said switches being located on opposite sides of the neutral position of said operator so that movement of said operator in a selected direction from its neutral position will operate a selected one or another of said switches to permit the opening of a selected one of the remote air and water control valves;
   (e) a third switch adjacent the second end of said support and operable to initiate the flow of spray upon movement of the second end of said support to its second limit of travel;
   (f) means associated with said operator for generating an electrical signal which varies in proportion to the distance moved by said operator from its neutral position, said signal being utilized to determine the amount of the opening of the selected control valve; and
   (g) bias means urging said operator to its neutral position and the second end of said support to its first limit of travel.

3. A dental syringe comprising:
   (a) a hand held housing;
   (b) a support within said housing, said support being hinge connected to said housing at one end so that a second end of said support can move vertically with respect to said housing between defined limits said second end having a clearance opening;
   (c) a control member carried by said support with at least a portion of said control member extending through an opening in said housing for manipulation by thumb or fingers of the hand holding said housing, said control member being movable with respect to said support to either side of a neutral position;
   (d) a pair of switches carried by said support and operatively connected to said control member so that movement of said control member in a selected direction from its neutral position will operate a selected one of said pair of switches to permit the flow of air or water from the syringe;
   (e) rate control means on said support and associated with said control member for generating an electrical signal proportionate to the distance said control member is moved from its neutral position, said signal being used to control the quantity of flow of air or water;
   (f) a stud fixed to said housing and extending through said clearance opening in said support;
   (g) a collar on said stud defining a first limit of travel for said support;
   (h) bias means urging the second end of said support against said collar; and
   (i) means for initiating the flow of spray and being operable when the second end of said support is moved against said bias by pushing said control member into said housing opening.

4. A dental syringe as in claim 3 including an elongated operator slidably carried by said support, said operator being operatively connected at one end to said control member and having a pair of bent sections each associated with one of said switches, each switch including a spring biased contact engaging against said bent sections to urge said control member to its neutral position.

5. A dental syringe as in claim 4 in which said control member is a wheel journaled to said support, said wheel having an off center pin captured in an elongated slot formed in said operator whereby rotation of said wheel to either side of its neutral position moves said operator through a linear path of travel for operating a selected one of said pair of switches.

6. A dental syringe as in claim 3 in which said rate control means comprises:
   (a) a magnet on said control member;
   (b) a Hall effect device on said support adjacent said magnet and positioned so that movement of said control member from its neutral position to operate a selected one of said pair of switches will change the electrical characteristics of said Hall effect device to produce said electrical signal.

7. In a multifunctional dental syringe for the selective joint or separate release of air and water including a first switch in a water control circuit, a second switch in the air control circuit and means for operating the first and second switches, the improvement comprising:

(a) a switch operator which can be moved to either side of a neutral position and which is biased to automatically return to its neutral position;

(b) signal generating means operating together with said switch operator for producing a signal representing the distance of said switch generator from its neutral position;

(c) said switch operator being the common operator for said first and second switches, one or another of said switches being operated responsive to movement of said switch operator in one direction or another respectively from its neutral position; and (d) said first and second switches, said signal generating means and said switch operator all being arranged as a unitary structure which functions as an actuator for a third switch to initiate the joint release of air and water.

* * * * *